(12) United States Patent
Kim et al.

(10) Patent No.: US 6,372,876 B1
(45) Date of Patent: Apr. 16, 2002

(54) USE OF POLYURETHANES WHICH ARE SOLUBLE OR DISPERSIBLE IN WATER AS AIDS IN COSMETIC AND PHARMACEUTICAL COMPOSITIONS, AND POLYURETHANES WHICH CONTAIN POLYLACTIC ACID POLYOLS AS COPOLYMERIZED UNITS

(75) Inventors: Son Nguyen Kim, Hemsbach; Axel Sanner, Frankenthal; Karin Sperling-Vietmeier, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/367,327

(22) PCT Filed: Jul. 17, 1999

(86) PCT No.: PCT/EP93/01888

§ 371 Date: Jan. 24, 1995

§ 102(e) Date: Jan. 24, 1995

(87) PCT Pub. No.: WO94/03510

PCT Pub. Date: Feb. 17, 1994

(30) Foreign Application Priority Data

Jul. 29, 1992 (DE) .......................... 42 26 045

(51) Int. Cl.[7] .............................. C08G 18/30
(52) U.S. Cl. .................. 528/71; 528/80; 424/486; 424/70.11; 424/DIG. 1; 132/202; 427/2.14
(58) Field of Search .................. 528/71, 80; 424/486, 424/70.11, DIG. 1; 132/202; 427/2.14

(56) References Cited

U.S. PATENT DOCUMENTS

| | | | |
|---|---|---|---|
| 3,412,054 A | * 11/1968 | Milligan | 524/591 |
| 3,658,939 A | 4/1972 | Carpenter et al. | |
| 3,835,081 A | * 9/1974 | Remley | 524/714 |
| 3,975,350 A | * 8/1976 | Hudgin et al. | 424/81 |
| 4,098,743 A | 7/1978 | Scriven et al. | |
| 4,147,679 A | 4/1979 | Scriven et al. | |
| 4,743,673 A | * 5/1988 | Johnston et al. | 528/60 |

FOREIGN PATENT DOCUMENTS

| | | | |
|---|---|---|---|
| DE | 1570615 | | 10/1965 |
| DE | 3814536 | * | 11/1988 |
| EP | 0039162 | * | 11/1981 |
| EP | 0043974 | * | 1/1982 |
| SU | 1016314 | | 12/1979 |

* cited by examiner

Primary Examiner—Rachel Gorr
(74) Attorney, Agent, or Firm—Oblon, Spivak, McClelland, Maier & Neustadt, P.C.

(57) ABSTRACT

The use of polyurethanes which are—soluble or dispersible in water and are composed of a) at least one compound which contains two or more active hydrogens per molecule, b) at least one diol containing acid groups or salt groups and c) at least one diisocyanate with a glass transition temperature of at least 15° C. and acid numbers of from 12 to 150 or the salts of these polyurethanes as aids in cosmetic and pharmaceutical compositions, and of polyurethanes which are soluble or dispersible in water and which contain (a) at least 5 mol % of a polycondensate of lactic acid and of a polyol of the formula

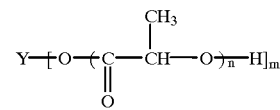

(IV)

where

Y is a radical derived from a dihydric to tetrahydric alcohol n is 1–50 and m is 1–4 as copolymerized units.

6 Claims, No Drawings

USE OF POLYURETHANES WHICH ARE SOLUBLE OR DISPERSIBLE IN WATER AS AIDS IN COSMETIC AND PHARMACEUTICAL COMPOSITIONS, AND POLYURETHANES WHICH CONTAIN POLYLACTIC ACID POLYOLS AS COPOLYMERIZED UNITS

The present invention relates to the use of polyurethanes which are soluble or dispersible in water and are composed of a) at least one compound which contains two or more active hydrogens per molecule,
b) at least one diol containing acid groups or salt groups and
c) at least one diisocyanate with a glass transition temperature of at least 15° C. and acid numbers of from 12 to 150 or the salts of these polyurethanes as aids in cosmetic and pharmaceutical compositions, and to polyurethanes which are soluble or dispersible in water.

Polyurethanes which are at least partially biodegradable and contain hydroxy carboxylic acid copolymerized units have been disclosed. Either they are insoluble in water, like the polyurethane from polylactic acid diol and diisocyanate disclosed in SU-A-1 016 314, or they form films which are too soft, like the polyurethanes from poly(ε-caprolactone diol)dimethylolpropionic acid and diisocyanates disclosed in U.S. Pat. No. 4,098,743 and U.S. Pat. No. 4,147,679.

Water-soluble polyurethanes which contain carboxyl-containing diols as copolymerized units are disclosed in U.S. Pat. No. 3,412,054 and U.S. Pat. No. 3,658,939. They are used as adhesives and in coatings and printing inks. Sulfonate- and/or carboxylate-containing polyurethanes which are dispersible in water are disclosed in DE-A-15 70 615. They are used, for example, for coating and impregnating textiles, leather, paper, wood and metals.

In cosmetics, hair-treatment compositions which are, for example, in the form of setting preparations or sprays are used for setting, improving the structure and shaping the hair. These compositions are composed mainly of a solution of film-forming resins or synthetic polymers. The following film formers have hitherto been mainly used in such compositions: shellac, homo- and copolymers of N-vinylpyrrolidone, copolymers of vinyl ethers and maleic monoesters, of (meth)acrylic acid or the esters and amides thereof and crotonic acid with vinyl esters.

The hair-treatment compositions are applied to the hair by spraying in the form of solutions, preferably in ethanol. After the solvent has evaporated, the hair is held in in the desired shape by the polymer remaining at the points of contact. The polymers must, on the one hand, be sufficiently hydrophilic to be washed out of the hair but, on the other hand, be hydrophobic so that hair treated with the polymers retains its shape and does not become sticky even when the humidity is high.

The polymeric film formers disclosed to date, such as polyvinylpyrrolidones, usually have the disadvantage of excessive uptake of water when the humidity is high. This property results, inter alia, in unwanted adhesion of the hair and in a loss of strength of the setting, and thus collapse of the hair style. If, on the other hand, the resistance to high humidity is improved, eg. with copolymers of N-vinylpyrrolidone and vinyl acetate, the elasticity of the film suffers, and the brittleness of these films after the treatment of the hair may even result in unpleasant dust formation and a flaky coating. In addition, there are great difficulties in particular with washing out of the hair. The above-mentioned synthetic hair-treatment compositions are not biodegradable because their C—C chain resists hydrolysis. Shellac is, on the other hand, biodegradable but has many disadvantages for the treatment of hair. Thus, its properties are not as good as those of the homo- and copolymers of N-vinylpyrrolidone, especially with regard to the adhesiveness, solubility in water and rigidity. Since shellac is a natural product, its properties are subject to wide variation.

It is an object of the present invention to provide aids for cosmetic and pharmaceutical compositions, as well as novel substances.

We have found that the first object is achieved by using polyurethanes which are soluble or dispersible in water and are composed of a) at least one compound which contains two or more active hydrogens per molecule,
b) at least one diol containing acid groups or salt groups and
c) at least one diisocyanate with a glass transition temperature of at least 15° C. and acid numbers of from 12 to 150 or the salts of these polyurethanes as aids in cosmetic and pharmaceutical compositions.

We have found that the other object is achieved by polyurethanes which are soluble or dispersible in water and are composed of a) at least one compound which contains two or more active hydrogens per molecule,
b) at least one diol containing acid groups or salt groups and
c) at least one diisocyanate with acid numbers of from 12 to 150 or the salts of this polyurethane, which contain as compounds in group (a) at least 5 mol % of a polycondensate of lactic acid and of a polyol of the formula

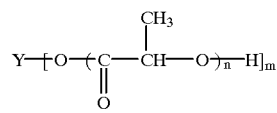

(IV)

where
Y is a radical derived from a dihydric to tetrahydric alcohol,
n is 1–50 and
m is 1–4,
as copolymerized units.

Suitable for the use according to the invention are all polyurethanes which are soluble or dispersible in water, contain the abovementioned components a) to c) as copolymerized units, and have a glass transition temperature of at least 15° C. and acid numbers of from 12 to 150, as well as the salts of the polyurethanes. Suitable compounds in group a) are all compounds which can be employed for preparing polyurethanes and have 2 or more active hydrogens per molecule. Examples of suitable compounds in group a) are diols, diamines, polyesterols, polyetherols or mixtures of said compounds, it being possible to replace up to 3 mol % of said compounds by triols or triamines. Examples of suitable diols are ethylene glycol, propylene glycol, butylene glycol, neopentyl glycol, polyetherols such as polyethylene glycols with molecular weights up to 3000, block copolymers of ethylene oxide and propylene oxide with number average molecular weights of up to 3000 or copolymers of ethylene oxide, propylene oxide and butylene oxide, which contain the alkylene oxide units distributed randomly or in the form of blocks. The diols and polyetherols preferably used are ethylene glycol, neopentyl glycol, diethylene glycol, triethylene glycol, tetraethylene glycol, pentaethylene glycol and hexaethylene glycol.

Examples of suitable diamines are ethylenediamine, propylenediamine, 1,4-diaminobutane and hexamethylenediamine, as well as α,ω-diamines which can be prepared by the amination of polyalkylene oxides, especially polyethylene oxides, with ammonia.

Also suitable as compounds in group a) are all polyesterols which are normally employed to prepare polyurethanes, eg. products of the reaction of phthalic acid and diethylene glycol, isophthalic acid and 1,4-butanediol, isophthalic acid/adipic acid and 1,6-hexanediol, and adipic acid and ethylene glycol.

Particularly suitable polyesterols are poly(α-hydroxy carboxylic acid diols) of the formula

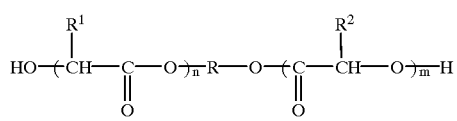
(I)

where $R^1$ and $R^2$ are each H, $C_1$–$C_5$-alkyl or aryl,

R is a radical derived from a diol (alkylene radical) with 2–8 carbons, n and m are each 1–30.

R in formula I is preferably —$CH_2$—$CH_2$—,

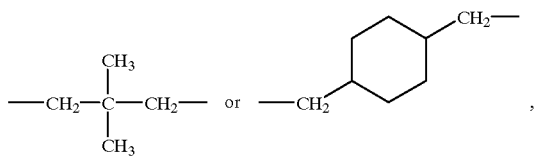

and $R^1$ and $R^2$ are preferably each $CH_3$.

Examples of α-hydroxy carboxylic acids which are suitable for preparing the poly(α-hydroxy carboxylic acid diols) are lactic acid, α-hydroxybutyric acid, lactide and glyoxylic acid. Lactic acid is preferably employed, and all the isomers are suitable: L-, D- and DL-lactic acid.

It is-also possible to use mixtures of compounds in group a) to prepare the polyurethanes, eg. mixtures of a diol and of a polyesterol, or of a diol and polyetherols. Up to 3 mol % of said compounds can be replaced by triols or triamines in the mixtures. Examples of suitable triols are glycerol, trimethylolethane or trimethylolpropane. Particularly suitable triamines are diethylenetriamine or dipropylenetriamine.

Compounds in group b) which can be employed to prepare the polyurethanes are all diols which contain acid groups or salt groups and are customary for this purpose. Particularly suitable are dimethylolpropanoic acid, compounds of the formula

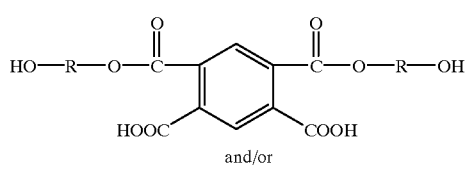
(II)

and/or

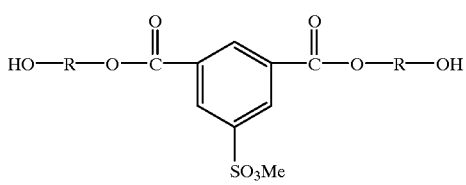
(III)

R in the formulae II and III is in each case a $C_2$–$C_{18}$-alkylene group and is preferably

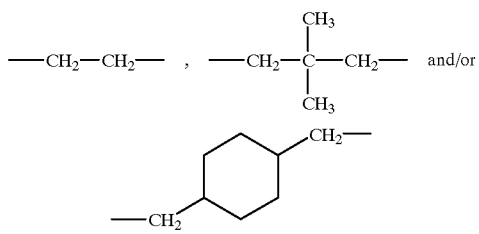
and/or

Me in formula III is Na or K.

The di- and polyisocyanates normally used can be used to prepare the polyurethanes. Particularly preferably used as compounds in group c) are hexamethylene diisocyanate, isophorone diisocyanate and/or toluylene diisocyanate. Chain extenders can be used as is customary in the preparation of polyurethanes. Examples of suitable chain extenders are hexamethylenediamine, piperazine, 1,2-diaminocyclohexane, 1,3-diaminocyclohexane, 1,4-diaminocyclohexane, neopentanediamine and 4,4'-diaminodicyclohexylmethane.

Biodegradable polyurethanes which are soluble or dispersible in water and contain as component a) at least 5 mol % of a polycondensate of lactic acid and of a polyol of the formula

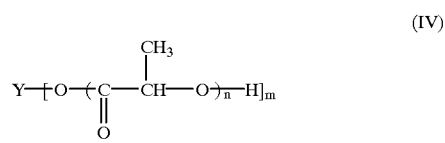
(IV)

where

Y is a radical derived from a dihydric to tetrahydric alcohol, n is 1–50 and m is 1–4, as copolymerized units are novel substances. Compounds of the formula IV can be obtained, for example, by esterifying a dihydric to tetrahydric alcohol with from 1 to 50 mol of lactic acid. Compounds in group a) which are preferably used are products of the reaction of diols with lactic acid, employing up to 50 mol, in particular from 5 to 30 mol, of lactic acid per mol of diol. Suitable examples of diols are ethylene glycol, propylene glycol, butylene glycol, neopentyl glycol and 1,6-hexanediol, as well as polyetherols such as diethylene glycol, triethylene glycol, tetraethylene glycol, pentaethylene glycol, copolymers of ethylene oxide and propylene oxide or copolymers of ethylene oxide, propylene oxide and butylene oxide, which may contain the alkylene oxide units in the form of blocks or in random distribution. The polyetherols have molecular weights up to 3000, preferably-up to 1000. The compounds of the formula IV can be used as component a) for preparing the novel polyurethanes either alone or mixed with other above-mentioned compounds of component a) which are normally employed to prepare polyurethanes. In mixtures of various compounds in group a) the compounds of the formula IV comprise at least 5, preferably at least 20, mol % of the mixture.

The above-mentioned novel polyurethanes can be obtained by reacting the compounds in groups a) and b) under an inert gas atmosphere in an inert solvent at from 70 to 130° C. with the compounds in group c). This reaction can, where appropriate, be carried out in the presence of chain extenders in order to prepare polyurethanes of higher molecular weight. As is customary in the preparation of polyurethanes, the molar ratio of the components [(a)+(b)]:(c) is from 0.8 to 1.1:1. The acid number of the polyurethanes is determined by the composition and the concentration of the compounds of component (b) in the mixture of components (a)+(b). The polyurethanes have Fikentscher K values (determined in 0.1% by weight solutions in N-methylpyrrolidone at 25° C. and pH 7) of from 15 to 100, preferably 25 to 50.

Substances which are likewise novel are biodegradable polyurethanes which are soluble or dispersible in water and which contain as component b) at least 5 mol % of a compound of the formula III

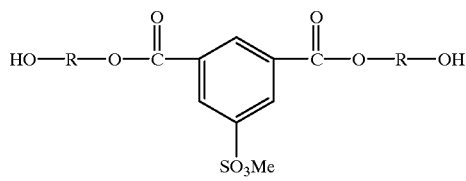

where R is a $C_2$–$C_{18}$-alkylene group and Me is Na or K, as copolymerized units.

All the polyurethanes described above are used according to the invention as aids in cosmetic and pharmaceutical compositions. The polyurethanes employed in the cosmetic and pharmaceutical sector have acid numbers of-from 12 to 150, preferably 30 to 90, and a glass transition temperature of at least 15° C. The glass transition temperature $T_g$ can be up to 120° C. and is preferably in the range from 30 to 100° C. The glass transition temperature is determined by the ASTM D 3418 method.

The polyurethanes after neutralization (partial or complete) are soluble in water or dispersible in water without the assistance of emulsifiers. As a rule, the salts of the polyurethanes, which can be obtained therefrom by neutralization with bases, are more readily soluble or dispersible in water than are the non-neutralized polyurethanes. Bases which can be used for neutralizing the polyurethanes are alkali metal bases such as sodium or potassium hydroxide solution, sodium carbonate or bicarbonate, potassium carbonate or bicarbonate and alkaline earth metal bases such as calcium hydroxide, calcium oxide, magnesium hydroxide or magnesium carbonate, and ammonia and amines. Particularly suitable for neutralizing the polyurethanes containing acid groups for use in hair-treatment compositions are 2-amino-2-methyl-propanol, diethylaminopropylamine and triisopropanolamine. The polyurethanes containing acid groups can also be neutralized with the aid of mixtures of bases, eg. mixtures of sodium hydroxide solution and triisopropanolamine. The neutralization can vary depending on the intended use from partial, eg. 20–40%, to complete, ie. 100%.

If the compounds according to the invention are dispersible in water they can be used in the form of aqueous microdispersions with particle diameters of, normally, 5–100 nm, in particular 10–80 nm, and solids contents of, normally, 1–40% by weight, in particular 3–30% by weight. These microdispersions do not as a rule require emulsifiers or surfactants to stabilize them.

The polyurethanes derived from lactic acid polyols are at least partially biodegradable. All the polyurethanes containing acid groups are at least 90% eliminated in sewage sludge (determined by the Zahn-Wellens method in DIN 38 412, part 25).

The polyurethanes described above are used not only in hair cosmetics but also in creams and in the drugs sector as tablet coating compositions and tablet binders. The novel substances described above, which contain as characteristic constituents at least one compound of the formula IV as copolymerized units, can furthermore be used as sizes and as adhesives which are soluble in water. Particularly suitable polyurethanes for use as adhesive are those which contain copolymerized units of the formula IV and have glass transition temperatures below 15° C. When the polyurethanes described above are used for hair treatment, they are usually employed in the form of aqueous or ethanolic solutions. The solids content of these solutions is from 0.1 to 30, preferably 1 to 15, % by weight of polyurethane or salt of a polyurethane.

EXAMPLES

General Preparation Method

Compounds a) and b) which are indicated in the table are dissolved in methyl ethyl ketone in a 4-necked flask which is equipped with stirrer, dropping funnel, thermometer, reflux condenser and means for operating under nitrogen. The mixture is then heated to about 80° C. while stirring. As soon as everything has dissolved, the mixture is cooled to about 50° C. and, while stirring, the diisocyanate indicated in the table under c) is added dropwise. The temperature increases during this. The mixture is then stirred at an internal temperature of 90° C. until the content of isocyanate groups remains virtually constant. The mixture is then cooled to from 10° C. to 30° C. and, at this temperature, the diamine indicated in the table is slowly added dropwise. The mixture is then stirred in this temperature range until the content of isocyanate groups has fallen to 0. If no chain extender is added, the remaining isocyanate groups are inactivated by adding amines, eg. 2-amino-2-methyl-1-propanol. Ethanol is then added, and most of the methyl ethyl ketone and of the ethanol is removed under reduced pressure at about 40° C. The remaining ethanol is removed in a vacuum oven at 50° C. The product after drying ranges from elastic to very hard and can be dissolved or dispersed in ethanol and in water, preferably after neutralization with an amine.

It is possible to add water, in place of ethanol, to the reaction mixture, and to neutralize the reaction product, eg. with an amine. The methyl ethyl ketone used as solvent can then be removed by distillation at 40° C. under reduced pressure so that an aqueous solution or dispersion of a polyurethane which contains acid groups and has the properties indicated in the table is obtained directly. The abbreviations in the table have the following meanings:

PEG300: polyethylene glycol MW=300 g/mol

NPG: neopentyl glycol

DMPA: dimethylolpropanoic acid

IPDI: isophorone diisocyanate
P(IPA/ADA-VI): polyesterol with MW=1000 g/mol from 2 5 isophthalic acid, adipic acid and hexanediol
P(ADA-DEG): polyesterol with MW=500 g/mol from adipic acid and diethylene glycol
P(PA-DEG): polyesterol with MW=450 g/mol from phthalic acid and diethylene glycol
P(LA-EG): polylactic acid-ethylene glycol MW=500 g/mol
P(PMDA-NPG): condensate of pyromellitic dianhydride and neopentyl glycol of molecular weight MW about 430 with the structure

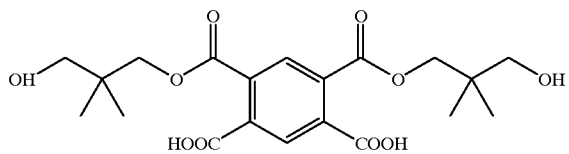

P(SIPA-NPG): condensate of the sodium salt of 5-sulfoisophthalic acid with neopentyl glycol of molecular weight MW about 440 and the structure

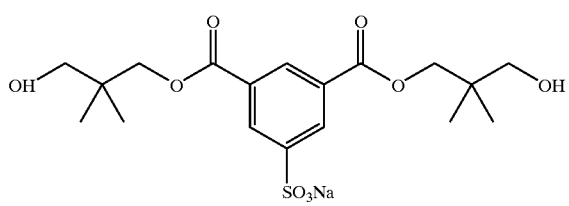

NMP: N-methylpyrrolidone
EtOH ethanol
s: readily soluble
disp: dispersible

The biodegradability of the polyurethanes was determined by the Zahn-Wellens method, DIN 38 412, part 25.

The polyurethanes 1 to 5 are prior art, whereas polyurethanes 6 and 7 are novel substances according to the invention.

In order to demonstrate the use for hair treatment, the following compositions were prepared:

| (a) Aerosol hair spray (in pure ethanol) | |
|---|---|
| polyurethane of Example 3 | 3% |
| 2-amino-2-methylpropanol | 0.26% |
| ethanol abs. | 61.74% |
| dimethyl ether | 35% |
| (b) Aerosol hair spray (aqueous alcoholic) | |
| polyurethane of Example 3 | 3.00% |
| 2-amino-2-methylpropanol | 0.26% |
| water dist. | 10.00% |
| ethanol abs. | 51.74% |
| dimethyl ether | 35.00% |
| (c) Manual pump spray | |
| polyurethane of Example 3 | 6.00% |
| 2-amino-2-methylpropanol | 0.52% |
| water dist. | 93.48% |
| (d) Hair setting composition (in pure water) | |
| polyurethane of Example 5 | 4.00% |
| 2-amino-2-methylpropanol | 0.37% |
| water dist. | 95.63% |
| (e) Hair setting composition (aqueous alcoholic) | |
| polyurethane of Example 5 | 4.00% |
| 2-amino-2-methylpropanol | 0.37% |
| water dist. | 63.75% |
| ethanol abs. | 31.88% |

TABLE

| | Composition [molar content] | | | |
|---|---|---|---|---|
| Polyurethane No. | Component (a) diol | Component (b) acid-containing diol | Component (c) diisocyanate | Diamine |
| 1 | PEG300 [1]; NPG [0.5] | DMPA [1.5] | IPDI [3.2] | piperazine [0.2] |
| 2 | P(ADA-DEG) [1] | DMPA [1.3] | IPDI [2.1] | — |
| 3 | P(IPA/ADA-VI) [1]; NPG [2] | DMPA [3] | IPDI [6] | — |
| 4 | P(IPA/ADA-VI) [1]; NPG [2] | DMPA [2.5] P(SIPA-NPG) [1] | IPDI [6.5] | piperazine [0.003] |
| 5 | P(PA-DEG) [1] | DMPA [1.5] | IPDI [2.7] | piperazine [0.03] |
| 6 | P(LA-EG) [1] | DMPA [2] | IPDI [2.7] | — |
| 7 | P(LA-EG) [1]; NPG [2] | (PMDA-NPG) [1] P(SIPA-NPG) [1] | IPDI [4.5] | — |

| Polyurethane No. | Acid number | $T_G$[1] [°C.] | K value 0.1% strength in NMP | Solubility[2] EtOH | Solubility[2] $H_2O$ | Curl retention (25° C., 90% rel. humidity, 5 h) | Biodegradability Zahn-Wellens |
|---|---|---|---|---|---|---|---|
| 1 | 62 | 68 | 37.4 | s | disp. | 54 | — |
| 2 | 68 | 62 | 26 | s | s | 35 | — |
| 3 | 54 | 71 | 32 | s | disp. | 86 | 94 |
| 4 | 50 | 88 | 34.4 | disp. | disp. | 88[3] | — |
| 5 | 58 | 70 | 32.7 | disp. | s | 75 | — |

TABLE-continued

| 6 | 84 | 86 | 28   | s | s | 32 | 91 |
| 7 | 45 | 71 | 26.5 | s | s | 39 | 97 |

[1])Glass transition temperature $T_G$: was determined by differential thermal analysis (ASTM D3418).
[2])The solubility was determined after neutralization to pH 7 with 2-amino-2-methylpropanol (5% strength solution, RT)
[3])The curl retention of polyurethane 4 was measured in ethanol:$H_2O$ (50:45).

We claim:
1. A method for treating hair, comprising applying to hair a polyurethane which is soluble or dispersible in water and is composed of
   a) at least one compound which contains two or more active hydrogens per molecule,
   b) at least one diol containing acid groups or salt groups and
   c) at least one diisocyanate with a glass transition temperature of at least 150° C. and acid numbers of from 12 to 150 or the salts of these polyurethanes, wherein at least 20 mol % of poly(α-hyroxy carboxylic acid diols) of the formula I

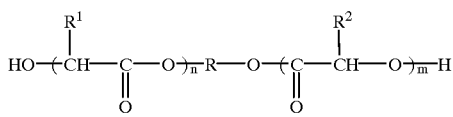

(I)

where
   $R^1$ and $R^2$ are each H, $C_1$–$C_5$-alkyl or aryl
   R is a radical derived from a diol (alkylene radical) with 2–8 carbons,
   n and m are each 1–30,
are used as compounds in group (a).
2. The method as claimed in claim 1, wherein dimethylolpropanoic acid, compounds of the formulae

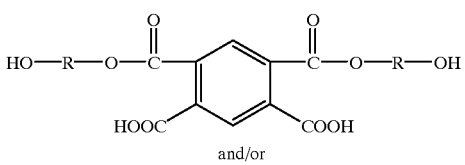

(II)

and/or

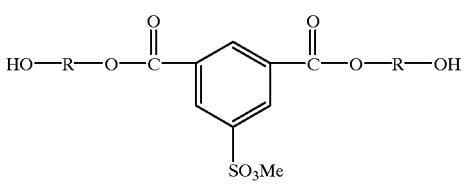

(III)

where R is in each case $C_2$–$C_{18}$-alkylene, and Me is Na or K, are used as compounds in group (b).
3. The method as claimed in claim 1, wherein hexamethylene diisocyanate, isophorone diisocyanate and/or toluylene diisocyanate are used as compounds in group (c).
4. A polyurethane which is soluble or dispersible in water and is composed of
a) at least one compound which contains two or more active hydrogens per molecule, b) at least one diol containing acid groups or salt groups and
c) at least one diisocyanate with acid numbers of from 12 to 150 or the salts of this polyurethane, which contains as compounds in group (a) at least 5 mol % of a polycondensate of lactic acid and of a polyol of the formula

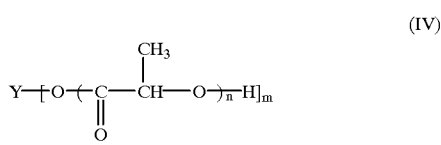

(IV)

where
   Y is a radical derived from a dihydric to tetrahydric alcohol,
   n is 1–50 and
   m is 1–4,
as copolymerized units.
5. A process for preparing the polyurethanes which are soluble or dispersible in water as claimed in claim 4, which comprises reacting the compounds in groups (a) and (b) under an inert gas atmosphere in an inert solvent at from 70 to 130° C. with the compounds in group (c), also optionally using conventional chain extenders.
6. A method for coating or binding a pharmaceutical composition, comprising coating or binding a pharmaceutical composition with a polyurethane which is soluble or dispersible in water and is composed of
   a) at least one compound which contains two or more active hydrogens per molecule,
   b) at least one diol containing acid groups or salt groups and
   c) at least one diisocyanate with a glass transition temperature of at least 15° C. and acid numbers of from 12 to 150 or the salts of these polyurethanes wherein at least 20 mol % of poly(α-hyroxy carboxylic acid diols) of the formula I

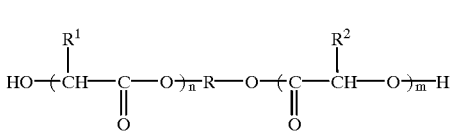

(I)

where
   $R^1$ and $R^2$ are each H, $C_1$–$C_5$-alkyl or aryl
   R is a radical derived from a diol (alkylene radical) with 2–8 carbons,
   n and m are each 1–30,
are used as compounds in group (a).

* * * * *

UNITED STATES PATENT AND TRADEMARK OFFICE
CERTIFICATE OF CORRECTION

PATENT NO. : 6,372,876 B1 Page 1 of 1
DATED : April 16, 2002
INVENTOR(S) : Kim et al.

It is certified that error appears in the above-identified patent and that said Letters Patent is hereby corrected as shown below:

<u>Title page,</u>
Item [22], the PCT information should read:
-- [22] PCT Filed     Jul. 17, 1993 --

Item [30], Foreign Application Priority information should read:
-- [30]     Foreign Application Priority Data
    Jul. 29, 1992   (DE) ................ P 42 25 045.5 --

Signed and Sealed this

Fifth Day of November, 2002

*Attest:*

JAMES E. ROGAN
*Attesting Officer*     *Director of the United States Patent and Trademark Office*